United States Patent [19]
Yokota et al.

[11] Patent Number: 5,540,887
[45] Date of Patent: Jul. 30, 1996

[54] TEST STRIP OVERTURNING MECHANISM IN AUTOMATED ANALYZER

[75] Inventors: Hiroshi Yokota; Keiji Takahashi, both of Hiratsuka, Japan

[73] Assignee: Bayer Corporation, Elkhart, Ind.

[21] Appl. No.: 422,259

[22] Filed: Apr. 14, 1995

[30] Foreign Application Priority Data

May 10, 1994 [JP] Japan .................................. 6-119735

[51] Int. Cl.$^6$ .................................................. G01N 35/10
[52] U.S. Cl. .................. 422/63; 422/64; 422/65; 436/43; 436/44; 436/46; 436/48
[58] Field of Search ................................. 422/63, 64, 65, 422/104; 436/43, 44, 46, 48

[56] References Cited

U.S. PATENT DOCUMENTS

| | | | |
|---|---|---|---|
| 3,549,232 | 12/1970 | Hugle | 350/90 |
| 3,848,962 | 11/1974 | Nelson | 350/86 |
| 4,279,514 | 7/1981 | Blümel et al. | 356/445 |
| 4,807,984 | 2/1989 | Kurimura et al. | 350/529 |
| 4,876,204 | 10/1989 | Inoue et al. | 436/46 |
| 5,298,425 | 3/1994 | Kuhn et al. | 436/43 |
| 5,356,595 | 10/1994 | Kanamori et al. | 422/65 |
| 5,415,840 | 5/1995 | Sano et al. | 422/67 |

*Primary Examiner*—James C. Housel
*Assistant Examiner*—Long V. Le
*Attorney, Agent, or Firm*—Roger N. Coe

[57] ABSTRACT

A test strip overturning mechanism in an automated analyzer for arranging test strips such that the right sides thereof may face in one direction, which comprises: an overturning device having an arm portion with suction holes being formed thereon; and a motor connected to the overturning device via a rotary shaft, wherein the suction holes formed on the arm portion are aligned in a straight line with suction holes formed on a transportation stage, arranged in the direction orthogonal to the direction that the test strips are moved; and a turntable is disposed at the position corresponding to the location of the arm portion when the overturning device is turned 180° around the rotary shaft.

1 Claim, 5 Drawing Sheets

TEST STRIP OVERTURNING MECHANISM IN AUTOMATED ANALYZER

BACKGROUND OF THE INVENTION

This invention relates to a test strip overturning mechanism in an automated analyzer, more specifically to a test strip overturning mechanism in an automated analyzer for arranging test strips such that the right sides of test pads may face in one direction, by discriminating the right sides of the test strips and then overturning them.

In the prior art, a test strip has been frequently used for testing a plurality of analysis items of a specimen such as urine easily and simply. As shown in FIG. 7, in a test strip 1, a plurality of test pads 3 impregnated with reagents are pasted on one end portion of a long and slender strip 2 made of plastic, and the other end portion is a holding portion 4. The respective specimen components (analytes) are analyzed by dipping the test strip 1 in a specimen to wet the test pads 3 and measuring coloration intensities of the test pads 3 at a light measuring portion of an analyzer.

In order to carry out the above operations automatically, the test strips 1 should be arranged such that the right sides of the test pads 3 face in one direction by the time when the test strips 1 are dipped in the specimens and supplied to the light measuring portion. The test strips 1 are contained in a test strip bottle such that the holding portions 4 may face to an opening, but the sides thereof do not face in one direction, i.e., the test pads 3 face in different directions. In order to realize full automation, it is required to incorporate a device for arranging the test strips 1 such that the right sides of the test pads 3 may face in one direction, into an analyzer.

SUMMARY OF THE INVENTION

An object of the present invention is to provide a test strip overturning mechanism in an automated analyzer, by which the right sides of test strips can be discriminated and then the test strips are overturned to be arranged such that the right sides of test pads may face in one direction and full automation can be realized if the mechanism of the present invention is employed in an automated analyzer in which a test strip bottle containing test strips is set as such and the test strips can directly be picked up from the test strip bottle.

As shown in FIG. 1 to FIG. 3, the test strip overturning mechanism in an automated analyzer for arranging test strips 1 such that the right sides thereof may face in one direction of the present invention comprises:

an overturning device 25 having an arm portion 26 with suction holes 27 being formed thereon; and a motor 30 connected to the overturning device 25 via a rotary shaft 31, wherein the suction holes 27 formed on the arm portion 26 are aligned in a straight line with suction holes 15 formed on a transportation stage 11, arranged in the direction orthogonal to the direction that the test strips 1 are moved; and a turntable 16 is disposed at the position corresponding to the location of the arm portion 26 when the overturning device 25 is turned 180° round the rotary shaft 31.

DESCRIPTION OF THE PREFERRED EMBODIMENTS

Figure 1:
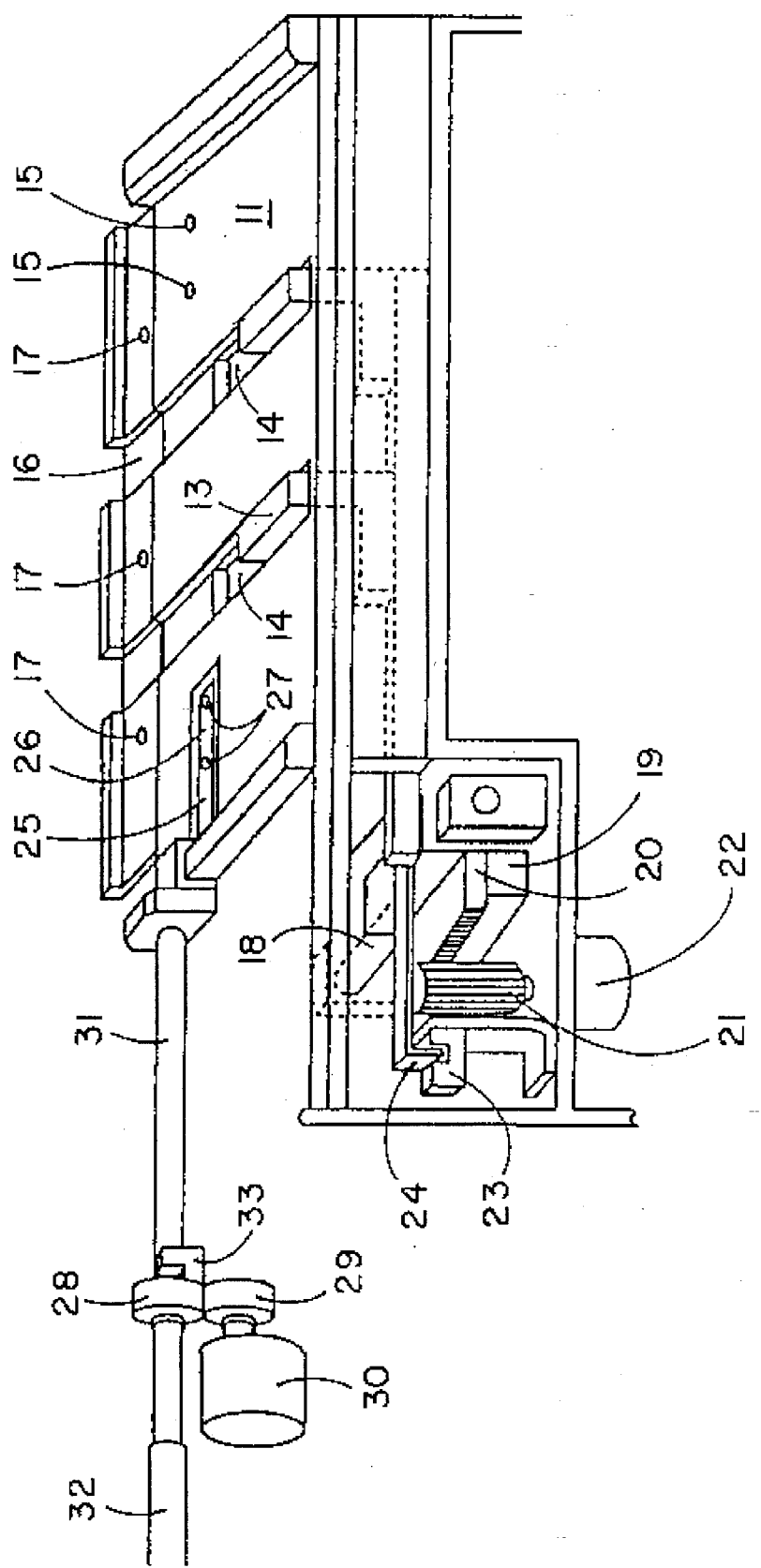
FIG. 1 is a perspective view showing the test strip overturning mechanism of the present invention.

In the following, the present invention is explained in detail.

The suction holes 27 formed on the arm portion 26 of the overturning device 25 are aligned in a straight line with the suction holes 15 formed on the transportation stage 11, arranged in the direction orthogonal to the direction that the test strip 1 is moved; and the turntable 16 is disposed at the position corresponding to the location of the arm portion 26 when the overturning device 25 is turned 180° round the rotary shaft 31. The right side of the test strip 1 is discriminated (i.e., determined) by the suction holes 15 on the transportation stage 11. When it is judged that the wrong side of the test strip 1 faces upward, the test strip 1 is adsorbed (i.e., held) to the arm portion 26 of the overturning device 25 at that position, and by turning the overturning device 25 180°, the test strip 1 can be disposed on the turntable 16 such that the right side thereof faces upward.

EXAMPLES

One embodiment of the test strip overturning mechanism in an automated analyzer of the present invention is described in detail by referring to the drawings.

Figure 2:
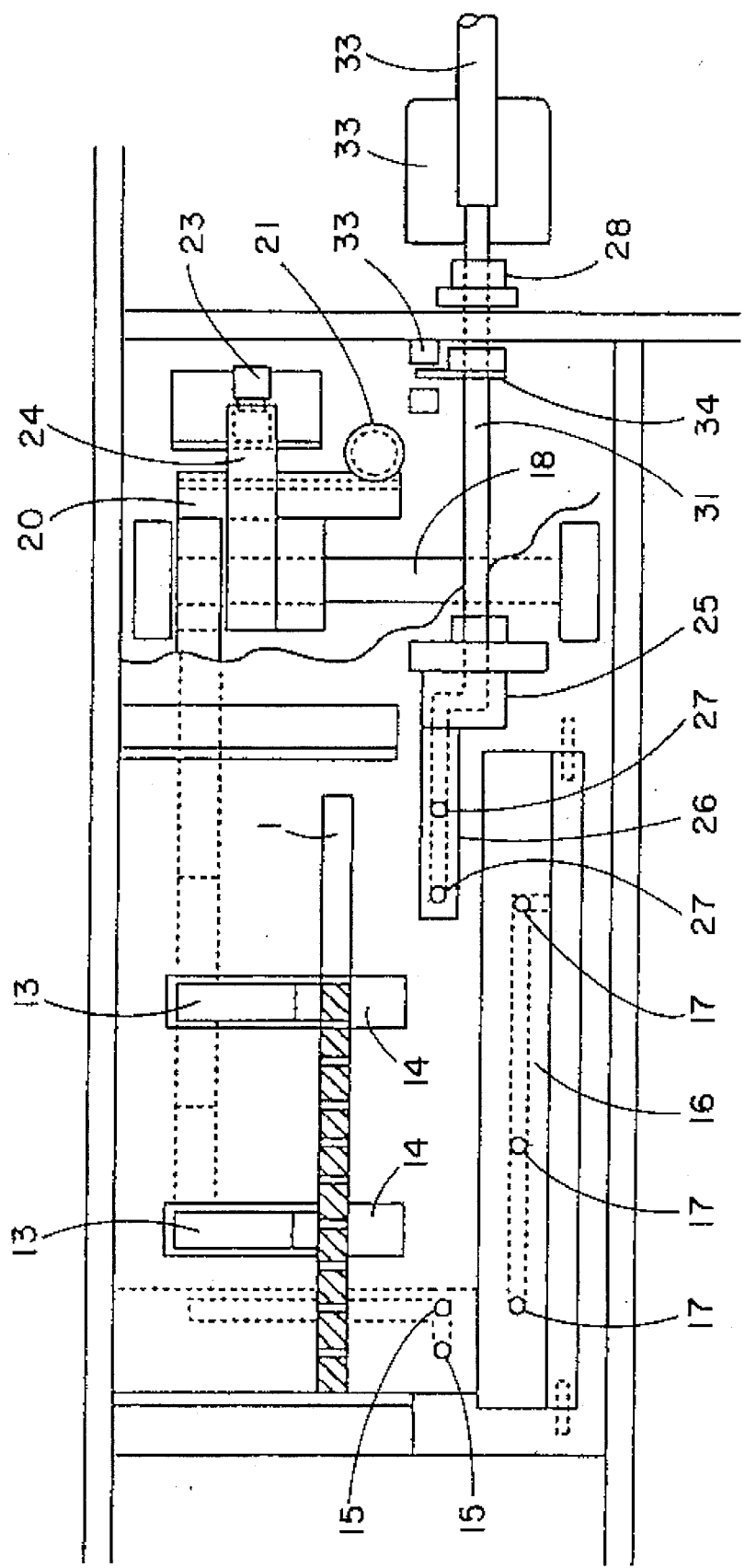
FIG. 2 is a plane view showing the test strip overturning mechanism of the present invention.
Figure 3:
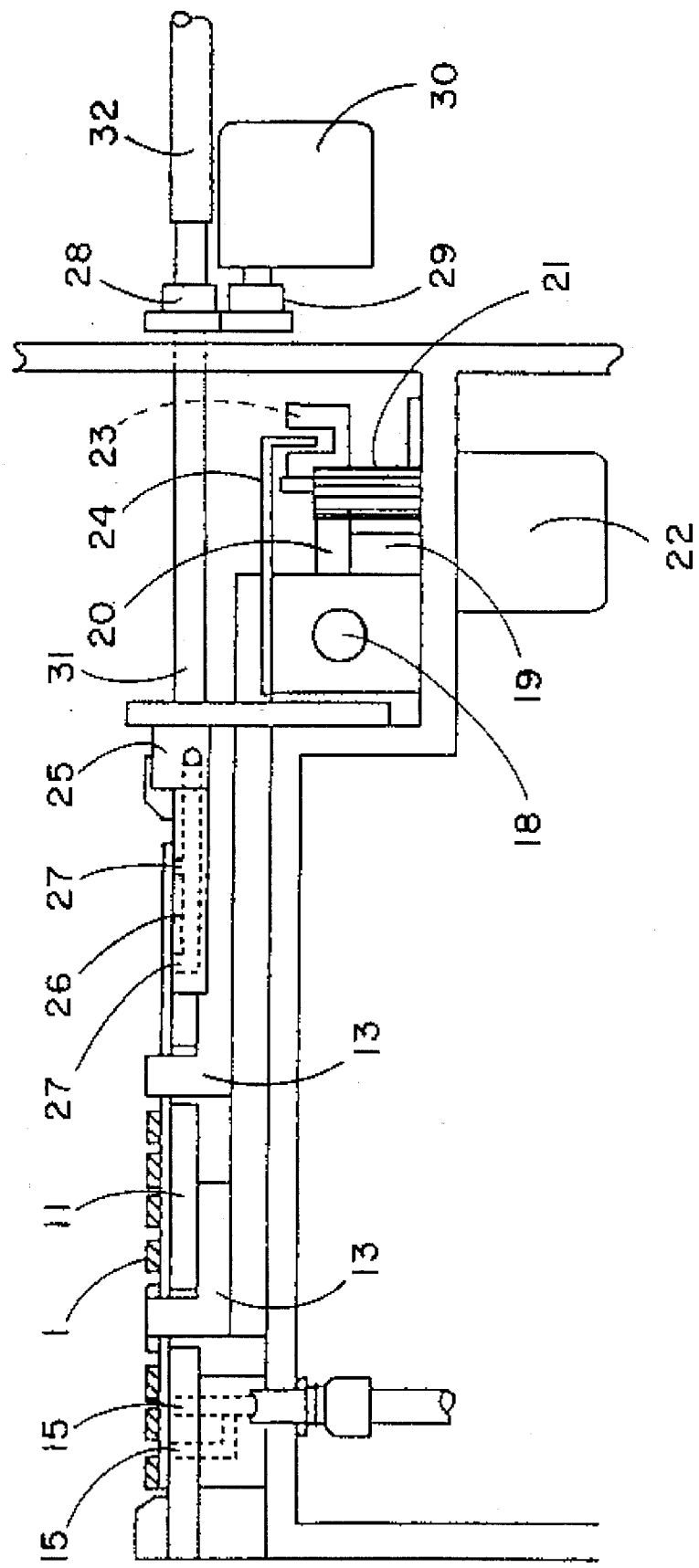
FIG. 3 is a side view showing the test strip overturning mechanism of the present invention.

As shown in FIG. 1 to FIG. 3, on the transportation stage 11 to which the test strip 1 picked up from a test strip bottle by being adsorbed to an air chuck is supplied, openings 14 are formed such that push bars 13 pushing the test strip 1 are movable. On the transportation stage 11, two of the suction holes 15 connected to a vacuum pump not shown in the figures are formed to be aligned in the direction orthogonal to the direction that the test strip 1 pushed by the push bars 13 is moved on the transportation stage 11, at the positions corresponding to the intervals between the test pads 3 of the test strip 1.

Three of the suction holes 17 on the turntable 16 are formed to be aligned in the direction orthogonal to the direction that the test strip 1 pushed by the push bars 13 is moved on the transportation stage 11, at the positions corresponding to the intervals between the test pads 3 of the test strip 1. The suction holes 17 have roles of discriminating the right side of the test strip 1 and holding the test strip 1 by adsorption such that the test strip 1 may not be displaced when it is transported to a next dipping step.

The push bars 13 are mounted on a movable member 19 which moves on a linear shaft 18. The movable member 19 is connected to a motor 22 via a rack 20 and a gear 21. A limit switch 23 and a flag mounted on the movable member 19 are provided for determining a stop position of the test strip 1.

In the L-shaped overturning device 25, two of the suction holes 27 are formed on the arm portion 26. The suction holes 27 are aligned in a straight line with the suction holes 15 formed on the transportation stage 11, arranged in the direction orthogonal to the direction that the test strip 1 is moved. On the overturning device 25 is mounted the hollow rotary shaft 31 connected to the motor 30 via a gear 28 and a gear 29. The other end of the rotary shaft 31 is connected to a vacuum pump not shown in the figures via a suction tube 32.

The turntable 16 disposed subsequent to the transportation stage 11 is disposed at the position corresponding to the location of the arm portion 26 when the overturning device 25 is turned 180° round the rotary shaft 31. A limit switch 33 and a flag 34 mounted on the rotary shaft 31 are provided for stopping the overturning device 25 at the position where it is turned 180°.

In the following, operations of the test strip overturning mechanism in an automated analyzer of the present invention are described in detail.

The test strip 1 picked up from a test strip bottle by being adsorbed to the air chuck is supplied on the transportation stage 11. Thereafter, the test strip 1 is pushed by the push bars 13 by actuating the motor 22 to be conveyed to the suction holes 15 on the transportation stage 11, and the motor 22 is stopped.

Then, the test strip 1 is sucked instantaneously (i.e., a vacuum measurement is made) to discriminate the right side of the test strip 1. When a specific vacuum degree is obtained, a detector not shown in the figures gives a signal that the right side of the test strip 1 faces upward. Then, the test strip 1 is pushed by the push bars 13 by actuating the motor 22 to be transported to the turntable 16.

Figure 4:
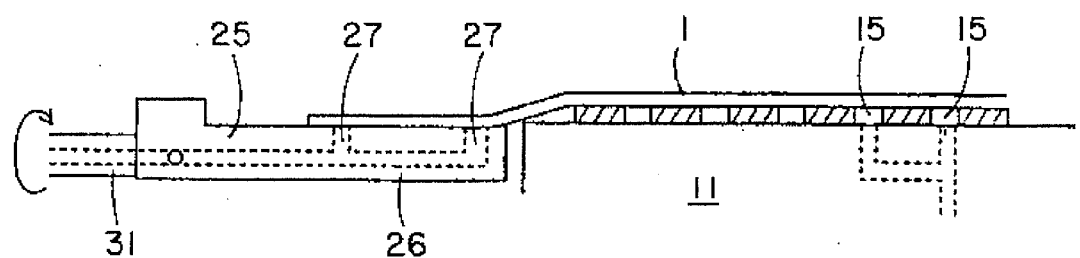
FIG. 4 is a view of illustrating operations of the test strip overturning mechanism.
Figure 5:
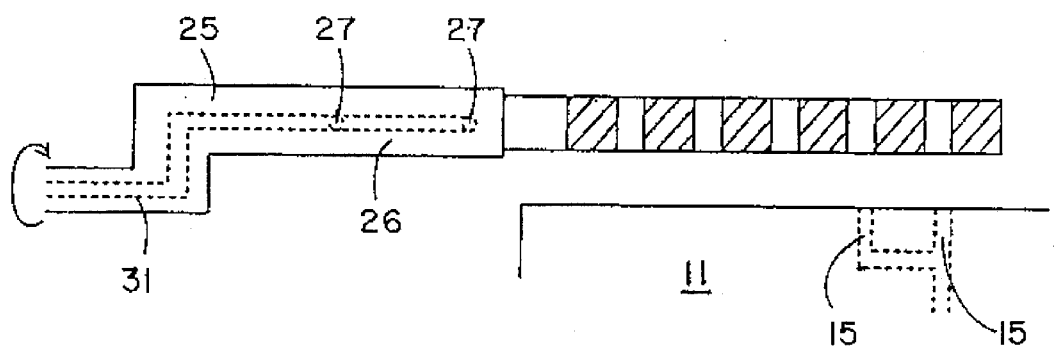
FIG. 5 is a view of illustrating operations of the test strip overturning mechanism.
Figure 6:
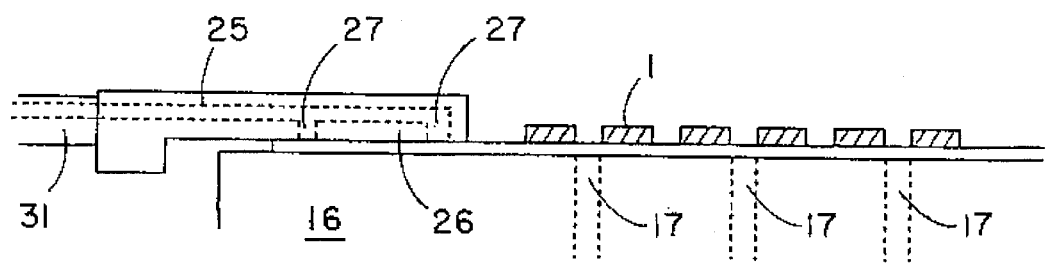
FIG. 6 is a view of illustrating operations of the test strip overturning mechanism.
Figure 7:
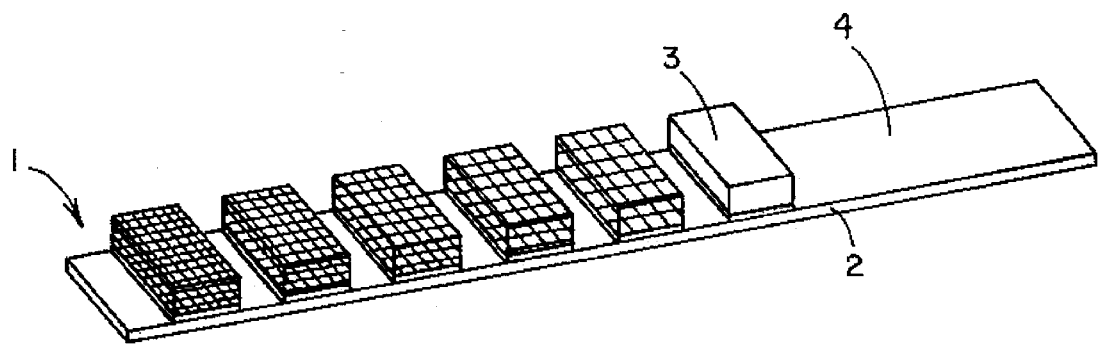
FIG. 7 is a perspective view of a test strip.

When a specific vacuum degree is not obtained and the detector gives a signal that the wrong side of the test strip 1 faces upward, the test strip 1 is adsorbed by the overturning device 25 (FIG. 4), the overturning device 25 is turned 180° by actuating the motor 30 (FIG. 5), and the test strip 1 is placed on the turntable 16 such that the right side thereof may face upward (FIG. 6).

Then, the test strip 1 is sucked instantaneously also on the turntable 16 to discriminate the right side of the test strip 1. When the detector gives a signal that the wrong side of the test strip 1 faces upward, the test strip 1 is returned from the turntable 16 to the transportation stage 11 by turning the overturning device 25 180° in a reverse direction by actuating the motor 30, and the right side of the test strip 1 is made face upward. After suction of the overturning device 25 is stopped, the test strip 1 is pushed by push bars 13 by actuating the motor 22 to be conveyed to the turntable 16.

On the turntable 16, the test strip 1 is sucked again instantaneously to discriminate the right side of the test strip 1. When the detector gives a signal that the wrong side faces upward, operations of the analyzer are interrupted. When the detector gives a signal that the right side of the test strip 1 faces upward, the test strip 1 is conveyed to a next test strip dipping step by lowering the turntable 16 by driving a motor not shown in the figures while the test strip 1 is adsorbed on the turntable 16. A next test strip is supplied on the transportation stage 11, and the operations described above are repeated.

According to the present invention, test strips on which reagent portions are present can be arranged such that the right sides thereof may face in one direction, so that the trouble of arranging the test strips beforehand such that the right sides thereof may face in one direction can be eliminated and full automation can be realized if the mechanism of the present invention is employed in, for example, an automated analyzer in which a container containing test strips is set as such and the test strips can directly be picked up from the container.

We claim:

1. A test strip overturning mechanism in an automated analyzer for arranging test strips such that right sides thereof may face in one direction, which comprises:

an overturning device having an arm portion with suction holes being formed thereon; and a motor connected to the overturning device via a rotary shaft, wherein the suction holes formed on the arm portion are aligned in a straight line with suction holes formed on a transportation stage, arranged in a direction orthogonal to a direction that the test strips are moved; and a turntable is disposed at a position corresponding to a location of the arm portion when the overturning device is turned 180° around the rotary shaft.

\* \* \* \* \*